United States Patent
Gyollai et al.

(10) Patent No.: US 7,145,017 B2
(45) Date of Patent: Dec. 5, 2006

(54) PREPARATION OF AZTREONAM

(75) Inventors: Viktor Gyollai, Debrecen (HU); Erzsebet Meszaros Sos, Debrecen (HU); Csaba Szabo, Debrecen (HU); Claude Singer, Kfar Saba (IL); Szabolcs Salyi, Debrecen (HU)

(73) Assignee: TEVA Gyógyszergyár Zártkörűen Működő Részvénytársaság, Debrecen (HU)

( * ) Notice: Subject to any disclaimer, the term of this patent is extended or adjusted under 35 U.S.C. 154(b) by 476 days.

(21) Appl. No.: 10/635,659

(22) Filed: Aug. 5, 2003

(65) Prior Publication Data

US 2004/0063682 A1    Apr. 1, 2004

Related U.S. Application Data

(60) Provisional application No. 60/400,699, filed on Aug. 5, 2002, provisional application No. 60/401,749, filed on Aug. 8, 2002.

(51) Int. Cl.
*C07D 277/20*    (2006.01)
(52) U.S. Cl. ...................... 548/194; 548/190
(58) Field of Classification Search ............... 548/190, 548/194
See application file for complete search history.

(56) References Cited

U.S. PATENT DOCUMENTS

| | | | |
|---|---|---|---|
| 4,529,698 A | 7/1985 | Sykes et al. | |
| 4,652,651 A | 3/1987 | Furlenmeier et al. | 548/194 |
| 4,775,670 A | 10/1988 | Sykes et al. | 514/210 |
| 4,826,973 A | 5/1989 | Anderson et al. | 540/355 |
| 4,923,998 A | 5/1990 | Takaya et al. | |
| 4,946,838 A | 8/1990 | Floyd et al. | 514/210 |
| 5,194,604 A | 3/1993 | Denzel et al. | 540/222 |
| 5,254,681 A | 10/1993 | Guanti et al. | 540/355 |
| 2004/0062721 A1 | 4/2004 | Montgomery | |
| 2005/0014739 A1 | 1/2005 | Gyollai et al. | |
| 2005/0032775 A1 | 2/2005 | Gyollai et al. | |

FOREIGN PATENT DOCUMENTS

| | | |
|---|---|---|
| EP | 0 070 024 A1 | 1/1983 |
| EP | 0 297 580 A1 | 1/1989 |
| PL | 165 700 B1 | 8/1993 |
| WO | WO 02/051356 A2 | 7/2002 |
| WO | WO 03/018578 A1 | 3/2003 |
| WO | WO 2004/052333 A1 | 6/2004 |

*Primary Examiner*—Golam M. M. Shameem
(74) *Attorney, Agent, or Firm*—Kenyon & Kenyon LLP

(57) ABSTRACT

The invention relates to a process for the synthesis of Aztreonam. Specifically, the process entails hydrolyzing [3S-[3α(Z),4β]]-3-[[(2-amino-4-thiazolyl)[(1-t-butoxycarbonyl-1-methylethoxy)imino]acetyl]amino]-4-methyl-2-oxo-1-azetidinesulfonic acid (t-Bu Aztreonam) to form Aztreonam.

13 Claims, No Drawings

PREPARATION OF AZTREONAM

CROSS-REFERENCE TO RELATED APPLICATIONS

This application claims the benefit under 35 U.S.C. §119 (e) of provisional application Ser. No. 60/400,699, filed Aug. 5, 2002 and provisional application Ser. No. 60/401,749, filed Aug. 8, 2002, both of which are incorporated herein by reference.

FIELD OF THE INVENTION

The present invention relates to a process for the synthesis of Aztreonam. Specifically, the process entails hydrolyzing [3S-[3α(Z),4β]]-3-[[(2-amino-4-thiazolyl)[(1-t-butoxycarbonyl-1-methylethoxy)imino]acetyl]amino]-4-methyl-2-oxo-1-azetidinesulfonic acid (t-Bu Aztreonam) to form Aztreonam.

BACKGROUND OF THE INVENTION

Aztreonam is a monobactam antibiotic disclosed in U.S. Pat. No. 4,775,670, which is incorporated by reference herein in its entirety. Aztreonam has the chemical name (Z)-2-[[[(2-amino-4-thiazolyl)[[(2S,-3S)-2-methyl-4-oxo-1-sulfo-3-azetidinyl]carbamoyl]methylene]amino]oxy]-2-methylpropionic acid. Aztreonam is also known as [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid and (2S, 3S)-3-[[2-[2-amino-4-thiazolyl]-(Z)-2[(1-carboxy-1-methylethoxy)imino]acetyl]amino]-4-methyl-2-oxo-1-azetidine-1-sulfonic acid.

Aztreonam has the structure:

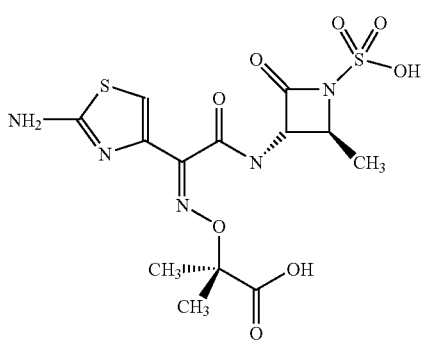

Aztreonam is known to exist in various polymorphic forms including the α, β, δ, and γ forms.

U.S. Pat. No. 4,775,670 discloses a process for making Aztreonam, a compound of formula I:

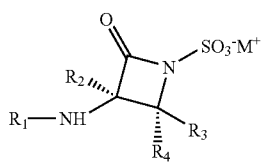

The process includes acylating a compound of formula IV:

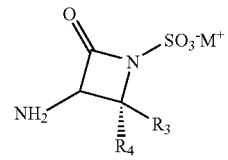

The acylation entails reacting a compound of formula IV with a carboxylic acid or the corresponding carboxylic acid halide or carboxylic acid anhydride ($R_1$—OH) in the presence of a carbodiimide such as dicyclohexylcarbodiimide and a substance capable of forming an active ester in situ such as N-hydroxybenzotriazole. U.S. Pat. No. 4,775,670 discloses that when the acyl group ($R_1$) contains reactive functional groups, such as amino or carboxyl groups, it may be necessary to first protect those functional groups, then carry out the acylation reaction, and finally deprotect the resulting product. The deprotection is carried out by reaction of the acylation product with trifluoroacetic acid in the presence of anisole under anhydrous conditions.

Similarly, U.S. Pat. No. 4,946,838 discloses a process for making crystalline anhydrous Aztreonam comprising reacting the diphenylmethyl ester of Aztreonam ([3S-[3β(Z), 4α]]-3-[[(2-amino-4-thiazolyl)[(1-diphenylmethoxycarbonyl-1-methylethoxy)imino]acetyl]amino]-4-methyl-2-oxo-1-azetidinesulfonic acid) with trifluoroacetic acid in the presence of anisole under anhydrous conditions to produce the α-form of Aztreonam. The α-form is recrystallized from an anhydrous organic solvent to produce the β-form of Aztreonam. The β-form is anhydrous, substantially non-hygroscopic and more stable than the α-form.

U.S. Pat. No. 5,254,681 discloses a process for preparing monobactams of formula (I):

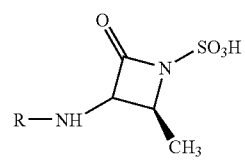

wherein R is acyl. The process comprises acylating azetidin with 2-(2-amino-4-thiazolyl)-2-(Z)-(alkoxyimino) acetic acid in the presence of 1-hydroxy-benzotriazole and dicyclohexylcarbodiimide.

U.S. Pat. No. 5,194,604 discloses a process and intermediates for making beta-lactams having aminothiazole(iminooxyacetic acid)acetic acid sidechains of formula (I), such as Aztreonam. The process comprises acylating a compound of formula III:

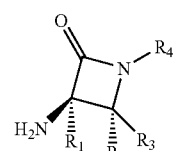

with a compound of formula (II):

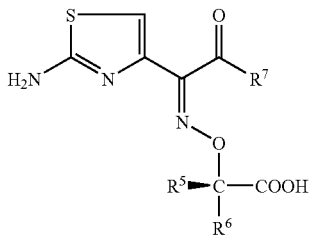

in which $R^7$ is

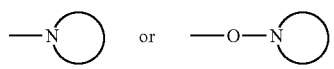

wherein

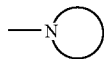

is a 4, 5, 6 or 7 membered heterocyclic ring having at least one nitrogen atom in the ring or such a group fused to a phenyl or substituted phenyl ring, to form a compound of formula (I):

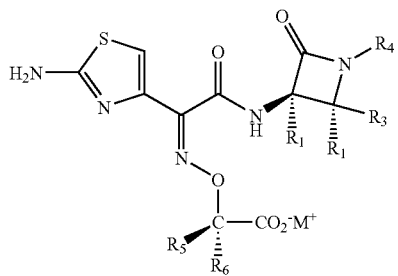

wherein $R_1$–$R_6$ are as defined in U.S. Pat. No. 5,194,604.

U.S. Pat. No. 4,652,651, which is incorporated by reference herein in its entirety, discloses a process for making 1-sulpho-2-oxoazetidine derivatives of the formula (I):

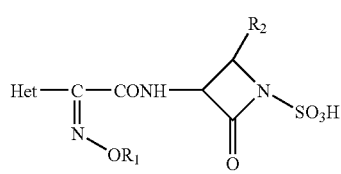

in which Het is an optionally amino-substituted, 5- or 6-membered, aromatic heterocycle containing 1 or 2 nitrogen atoms and optionally also an oxygen or sulphur atom, $R_1$ may be lower alkoxycarbonyl-lower alkyl and $R_2$ may be lower alkyl. The process entails acylating a compound of formula (II):

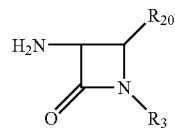

in which $R_{20}$ equals $R_2$ and $R_3$ is hydrogen or sulpho, with a thioester of the formula (III):

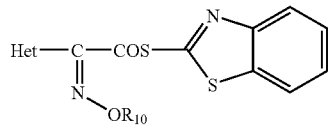

in which Het is as above and $R_{10}$ has any of the values of $R_1$. U.S. Pat. No. 4,652,651 discloses that where R10 is a lower alkoxycarbonyl-lower alkyl group, for example the t-butoxycarbonylmethyl group, this can be converted, if desired, into the corresponding carboxylower alkyl group by treatment with a strong acid such as trifluoroacetic acid (optionally in the presence of anisole), hydrochloric acid or p-toluenesulphonic acid at a low temperature such as −10° C. to room temperature.

There remains a need in the art for a process of making Aztreonam which does not require anhydrous reaction conditions and which also enables high yield and high purity. The present invention answers this need.

SUMMARY OF THE INVENTION

The invention is based on the discovery that Aztreonam can be produced by reacting [3S-[3α(Z),4β]]-3-[[(2-amino-4-thiazolyl)[(1-t-butoxycarbonyl-1-methylethoxy)imino]acetyl]amino]-4-methyl-2-oxo-1-azetidinesulfonic acid with aqueous acid. The process of the invention, enables yields of between 70–75% and purities above 98%, preferably above 99%. The inventive aqueous process is advantageous over the prior art anhydrous processes in that the reaction conditions are more mild, there is no need to clean the final product and there is no need to keep the system dry. Thus, the aqueous process is less expensive than the anhydrous processes.

The present invention is directed to a process for preparing [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid by hydrolyzing the ester group of [3S-[3α(Z),4β]]-3-[[(2-amino-4-thiazolyl)[(1-t-butoxycarbonyl-1-methylethoxy)imino]acetyl]amino]-4-methyl-2-oxo-1-azetidinesulfonic acid. The hydrolysis may be effected by reacting the ester with aqueous acid, at elevated temperatures.

One reaction scheme for carrying out the process is shown below:

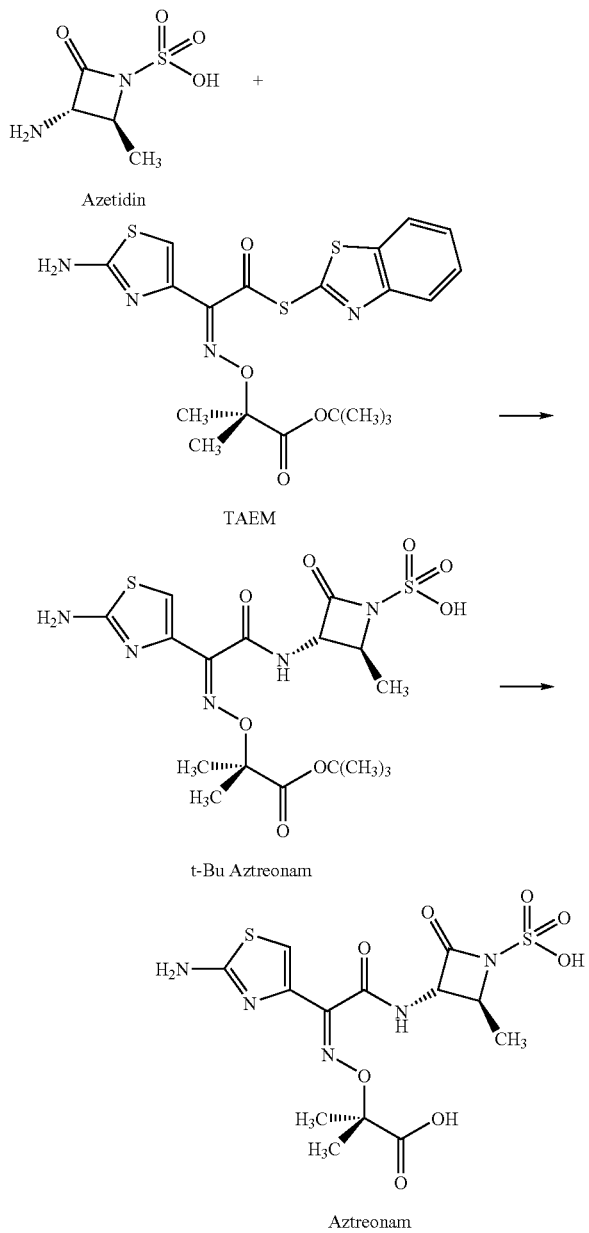

DETAILED DESCRIPTION OF THE INVENTION

The invention is directed to a process for making Aztreonam comprising reacting [3S-[3α(Z),4β]]-3-[[(2-amino-4-thiazolyl)[(1-t-butoxycarbonyl-1-methylethoxy)imino] acetyl]amino]-4-methyl-2-oxo-1-azetidinesulfonic acid also known as (t-Bu Aztreonam and Aztreonam t-butyl ester) with an aqueous acid at elevated temperatures.

The aqueous acid is preferably a mineral acid, such as hydrochloric acid or sulfuric acid, of various concentration. The aqueous mineral acid is preferably more concentrated than 0.1 mol/l. Preferably, the aqueous acid is a 1:1 v/v HCl:water mixture. Aqueous trifluoroacetic acid may also be used in various concentrations.

The hydrolysis reaction is carried out at elevated temperatures, preferably 40° C. or greater, more preferably between 50 and 80° C., and most preferably between 60 and 70° C.

The Aztreonam t-butyl ester can be obtained by reacting Azetidin, (3S,4S)-3-Amino-4-methyl-2-oxo-azetidine-1-sulfonic acid, with TAEM ((Z)-2-(2-Aminothiazole-4-yl)-2-(t-butoxycarbonyl)-isopropoxyimino acetic acid, benzothiazole-2-yl-thiolester), as illustrated in Examples 1 and 2.

The present invention is illustrated in further detail with reference to the following non-limiting examples.

EXAMPLE 1

5.4 g Azetidin is dissolved in 20 ml acetonitrile (or dimethyl formamide) with the assistance of 5 ml of triethylamine at room temperature. The solution is cooled to 0° C. A solution of 4 g TAEM in 25 ml THF is added with magnetic stirring. If the color disappears, 8 g TAEM in 50 ml THF is added. After 10 minutes, another 4.1 g TAEM in 25 ml THF is added. The solution is stirred at 0° C. for an additional hour. The pH is adjusted to about 4–5 with a freshly prepared TFA solution (TFA-THF 1:4, V/V). Being careful not to evaporate the acetonitrile, the THF is evaporated (weight loss is about 90 g) at 30° C. under vacuum. The remaining residue is diluted with 200 ml ethylacetate and then extracted with 100 ml and then 50 ml of distilled water. The aqueous extracts are combined and washed twice with 50 ml ethylacetate after readjustment of the pH to about 4–5. The dissolved ethylacetate is removed from the aqueous phase by vacuum at 30° C. 10–15 g KCl (or NaCl) is dissolved. The solution is acidified with HCl solution (cc. HCl-distilled water 1:4, V/V) with stirring (approx. 10 ml). The solution is cooled to 0° C. with slow stirring and crystallization occurs. The resulting suspension is refrigerated overnight (at about 5° C.). The suspension is filtered on a glass filter, and the crystals are washed with chilled water. The washed crystals are dried at room temperature. The product, Aztreonam t-butyl ester, is about 12.5–13 g white solid, which is sufficiently pure for the next step.

EXAMPLE 2

65 g Azetidine is dissolved in a mixture of 240 ml acetonitrile and 60 ml triethylamine. When dissolution is complete, TAEM is added in four portions. The suspension is stirred for 20–30 min, then diluted with 500 ml EtOAc and 500 ml water and stirred for 5–10 min. The pH of the emulsion is set to 5 with 2.4 M HCl solution. After the phases separate, the pH of the aqueous phase is checked. If the pH is between 4.20 and 5.30, the two phases are filtered and separated, otherwise more HCl is added. The upper phase is diluted with 900 ml ethylacetate and extracted with 2×500 ml water (faster phase separation). The combined aqueous phase is diluted with 500 ml water and washed with 2×500 ml ethylacetate. The dissolved ethylacetate is removed from the aqueous phase by vacuum. The aqueous phase is acidified further to pH 2 with 2.4 M HCl solution. The solution is stirred and cooled. Crystallization starts soon. The suspension is stirred and cooled to 0° C., stirring at this temperature overnight. The suspension is filtered, washed with chilled water, dried at 38° C. in air-circulated oven for 3 h. The yield is approx. 116–120 g of Aztreonam t-butyl ester.

EXAMPLE 3

Aztreonam t-butyl ester (113.6 g, 0.231 mol) is suspended in 975 ml water at 60° C. with stirring and 325 ml trifluoroacetic acid is added. The solution is stirred for 60 min., then it is cooled slowly using an ice-water bath. After the product precipitates, the suspension is refrigerated overnight. The product is filtered on a glass-filter, suspended in 240 ml chilled water and filtered again. The filtrate is re-suspended in 360 ml cold acetone and filtered. The latter step is repeated and the product is dried at room temperature to yield 61.6 g Aztreonam (water content: 15–16%).

EXAMPLE 4

Aztreonam t-butyl ester (18.0 g, 0.0366 mol) is suspended in 144 ml water at 60° C. with stirring and 40 ml aqueous hydrochloric acid (1:1, V/V) is added. The solution is stirred for 60 min, then 37 ml 5.4 M NaOH solution is added. The solution is cooled slowly using an ice-water bath. After the product precipitates, the suspension is refrigerated overnight. The product is filtered on a glass-filter, suspended in 50 ml chilled water and filtered again. The filtrate is re-suspended in 70 ml cold acetone and filtered. The latter step is repeated and the product is dried at room temperature to yield 8.3 g Aztreonam (water content: 15–16%). The crude Aztreonam is crystallized.

EXAMPLE 5

Aztreonam t-butyl ester (100.00 g, Assay as is: 97.2%, 0.19796 mol)) is suspended in a mixture of 450 ml water and 5 ml trifluoroacetic acid. The suspension, which slowly becomes clear, is heated to 58° C. with stirring and 100 ml trifluoroacetic acid is added. The solution is stirred for 105 min at 60–63° C. The solution is added to chilled water (450 ml) with efficient stirring and the resulting slurry is cooled further to 25° C. After two hours it is cooled to 0° C. and stirred for 18 hours. The product is filtered on a glass-filter and washed with 300 ml chilled water. The product is suspended in 650 ml chilled water, then filtered and washed with 300 ml cold acetone. The product is suspended in 400 ml cold acetone and filtered and dried in an air-ventilation oven at 30° C. for 30 min. Yield: 66.6 g (63%, according to assays) Aztreonam (Assay: 100.5%, water content: 18.0%).

HPLC Impurity Profile:
Aztreonam: 99.22%
Aztreonam t-butyl ester: 0.44%

HPLC Impurity Profile of Sample from Reaction Mixture:
Aztreonam: 82.20%
Aztreonam t-butyl ester: 0.43%
Aztreonam, open-chained: 7.22%
Other main degradation product (RRT=0.56): 5.24%

EXAMPLE 6

Aztreonam t-butyl ester (27.11 g, Assay as is: 96.5%, 0.05328 mol) is suspended in a mixture of 122 ml water and 1.35 ml cc. HCl. The suspension is heated to 62° C. with stirring and 30 ml cc. HCl is added. The suspension, which becomes clear after approx. 15 min, (then the product starts to precipitate), is stirred for 30 min at 63–65° C. Chilled water (162 ml) is added with efficient stirring and the resulting slurry is cooled further to 25° C. After two hours it is cooled to 0° C. and stirred for 2 hours. The product is filtered on a glass-filter, washed twice with 120 ml chilled water, twice with 125 ml cold acetone and filtered. The product is dried at room temperature overnight. Yield: 19.44 g (72%, according to assays) Aztreonam (Assay: 100.1%, water content: 14.4%).

HPLC Impurity Profile:
Aztreonam: 99.65%
Aztreonam t-butyl ester: 0.21%

HPLC Impurity Profile of Sample from Reaction Mixture:
Aztreonam: 89.43%
Aztreonam t-butyl ester: 0.26%
Aztreonam, open-chained: 4.70%
Other main degradation product (RRT=0.56): 1.47%

Having thus described the invention with reference to particular preferred embodiments and illustrated it with examples, those of skill in the art may appreciate modifications to the invention as described and illustrated that do not depart from the spirit and scope of the invention as disclosed in the specification.

What is claimed is:

1. A process for making Aztreonam comprising reacting [3S-[3α(Z),4β]]-3-[[(2-amino-4-thiazolyl)[(1-t-butoxycarbonyl-1-methylethoxy)imino]acetyl]amino]-4-methyl-2-oxo-1-azetidinesulfonic acid (t-Bu Aztreonam) with an aqueous acid.

2. The process of claim 1, wherein the acid is a mineral acid.

3. The process of claim 2, wherein the mineral acid is selected from the group consisting of hydrochloric acid, sulfuric acid and trifluoroacetic acid.

4. The process of claim 2, wherein the aqueous mineral acid has a concentration greater than 0.1 mole/liter.

5. The process of claim 3, wherein the mineral acid is hydrochloric acid.

6. The process of claim 3, wherein the mineral acid is trifluoroacetic acid.

7. The process of claim 1, wherein the aqueous acid is a 1:1 v/v HCl:water mixture.

8. The process of claim 1, wherein the reaction takes place at a temperature greater than about 40° C.

9. The process of claim 8, wherein the temperature is between about 50° C. to about 80° C.

10. The process of claim 9, wherein the temperature is between about 60° C. to about 70° C.

11. The process of claim 1, wherein the yield of Aztreonam is at least about 70%.

12. The process of claim 1, wherein the purity of Aztreonam, as measured by HPLC, is greater than about 98%.

13. The process of claim 1, wherein the purity of Aztreonam, as measured by HPLC, is greater than about 99%.

* * * * *

UNITED STATES PATENT AND TRADEMARK OFFICE
CERTIFICATE OF CORRECTION

PATENT NO. : 7,145,017 B2  Page 1 of 1
APPLICATION NO. : 10/635659
DATED : August 5, 2003
INVENTOR(S) : Viktor Gyollai et al.

It is certified that error appears in the above-identified patent and that said Letters Patent is hereby corrected as shown below:

Column 2,
Line 28, change "3β" to --3α--;
Line 29, change "4α" to --4β--;
Line 49, change "azetidin" to --azetidine--.

Column 5,
Line 12, change "Azetidin" to --Azetidine--.

Column 6,
Line 8, change "Azetidin" to --Azetidine--;
Line 18, change "Azetidin" to --Azetidine--;
Line 20, change "lamine" to --amine--.

Signed and Sealed this

First Day of April, 2008

JON W. DUDAS
*Director of the United States Patent and Trademark Office*

UNITED STATES PATENT AND TRADEMARK OFFICE
CERTIFICATE OF CORRECTION

PATENT NO. : 7,145,017 B2  Page 1 of 1
APPLICATION NO. : 10/635659
DATED : December 5, 2006
INVENTOR(S) : Viktor Gyollai et al.

It is certified that error appears in the above-identified patent and that said Letters Patent is hereby corrected as shown below:

Column 2,
Line 28, change "3β" to --3α--;
Line 29, change "4α" to --4β--;
Line 49, change "azetidin" to --azetidine--.

Column 5,
Line 12, change "Azetidin" to --Azetidine--.

Column 6,
Line 8, change "Azetidin" to --Azetidine--;
Line 18, change "Azetidin" to --Azetidine--;
Line 20, change "lamine" to --amine--.

This certificate supersedes the Certificate of Correction issued April 1, 2008.

Signed and Sealed this

Sixth Day of May, 2008

JON W. DUDAS
*Director of the United States Patent and Trademark Office*